United States Patent
Govea et al.

(10) Patent No.: US 9,775,988 B2
(45) Date of Patent: Oct. 3, 2017

(54) ELECTRICAL STIMULATION LEADS WITH HELICALLY ARRANGED ELECTRODES AND METHODS OF MAKING AND USING

(71) Applicant: BOSTON SCIENTIFIC NEUROMODULATION CORPORATION, Valencia, CA (US)

(72) Inventors: Andrew Govea, San Diego, CA (US); Joshua Dale Howard, Chatsworth, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 77 days.

(21) Appl. No.: 14/557,211

(22) Filed: Dec. 1, 2014

(65) Prior Publication Data

US 2015/0151113 A1    Jun. 4, 2015

Related U.S. Application Data

(60) Provisional application No. 61/910,678, filed on Dec. 2, 2013.

(51) Int. Cl.
| | | |
|---|---|---|
| A61N 1/00 | (2006.01) |
| A61N 1/05 | (2006.01) |
| B29C 70/68 | (2006.01) |
| B29C 70/78 | (2006.01) |
| B29C 70/84 | (2006.01) |
| B29K 101/12 | (2006.01) |

(52) U.S. Cl.
CPC ......... *A61N 1/0551* (2013.01); *A61N 1/0534* (2013.01); *B29C 70/682* (2013.01); *B29C 70/78* (2013.01); *B29C 70/84* (2013.01); *B29K 2101/12* (2013.01); *B29K 2995/0056* (2013.01)

(58) Field of Classification Search
CPC ............................ A61N 1/0551; A61N 1/0534
USPC .......................................................... 607/116
See application file for complete search history.

(56) References Cited

U.S. PATENT DOCUMENTS

| | | |
|---|---|---|
| 4,602,624 A | 7/1986 | Naples et al. |
| 4,630,611 A | 12/1986 | King |
| 4,744,370 A | 5/1988 | Harris |

(Continued)

FOREIGN PATENT DOCUMENTS

| | | |
|---|---|---|
| EP | 0580928 A1 | 2/1994 |
| EP | 0650694 B1 | 7/1998 |

(Continued)

OTHER PUBLICATIONS

International Search Report and Written Opinion for PCT/US2014/067971 dated Mar. 3, 2015.

*Primary Examiner* — Nadia A Mahmood
(74) *Attorney, Agent, or Firm* — Lowe Graham Jones PLLC; Bruce E. Black

(57) ABSTRACT

A stimulation lead can include segmented electrodes arranged in a single or double helix or other helical arrangement. In one method of manufacture, an electrode carrier with segmented electrode receiving openings is used. Another method employs a connected framework of helically arranged pre-electrodes that are separated during manufacture. Yet another method employs a mold to generate a planar carrier over the segmented electrodes followed by rolling the carrier into a cylinder. A further method includes forming an electrode assembly by alternative segmented electrodes with non-conducting spacers.

16 Claims, 12 Drawing Sheets

(56) References Cited

U.S. PATENT DOCUMENTS

| | | |
|---|---|---|
| 5,000,194 A | 3/1991 | van den Honert et al. |
| 5,135,001 A | 8/1992 | Sinofsky et al. |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,181,969 B1 | 1/2001 | Gord |
| 6,322,559 B1 | 11/2001 | Daulton et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,609,029 B1 | 8/2003 | Mann et al. |
| 6,609,032 B1 | 8/2003 | Woods et al. |
| 6,678,564 B2 | 1/2004 | Ketterl et al. |
| 6,741,892 B1 | 5/2004 | Meadows et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,203,548 B2 | 4/2007 | Whitehurst et al. |
| 7,244,150 B1 | 7/2007 | Brase et al. |
| 7,292,890 B2 | 11/2007 | Whitehurst et al. |
| 7,450,997 B1 | 11/2008 | Pianca et al. |
| 7,489,971 B1 | 2/2009 | Franz |
| 7,668,601 B2 | 2/2010 | Hegland et al. |
| 7,672,734 B2 | 3/2010 | Anderson et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,809,446 B2 | 10/2010 | Meadows |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,175,710 B2 | 5/2012 | He |
| 8,224,450 B2 | 7/2012 | Brase |
| 8,225,504 B2 | 7/2012 | Dye et al. |
| 8,271,094 B1 | 9/2012 | Moffitt et al. |
| 8,295,944 B2 | 10/2012 | Howard et al. |
| 8,321,025 B2 | 11/2012 | Bedenbaugh |
| 8,359,107 B2 | 1/2013 | Pianca et al. |
| 8,364,278 B2 | 1/2013 | Pianca et al. |
| 8,391,985 B2 | 3/2013 | McDonald |
| 8,583,237 B2 | 11/2013 | Bedenbaugh |
| 8,688,235 B1 | 4/2014 | Pianca et al. |
| 2001/0023368 A1 | 9/2001 | Black et al. |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0247697 A1 | 11/2006 | Sharma et al. |
| 2007/0150036 A1 | 6/2007 | Anderson |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0215125 A1 | 9/2008 | Farah et al. |
| 2008/0255647 A1 | 10/2008 | Jensen et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0276021 A1 | 11/2009 | Meadows et al. |
| 2010/0030298 A1 | 2/2010 | Martens et al. |
| 2010/0036468 A1 | 2/2010 | Decre et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1* | 1/2011 | Pianca ................. A61N 1/05 29/825 |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1* | 8/2012 | Pianca ................. A61N 1/0534 607/148 |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |
| 2013/0105071 A1 | 5/2013 | DiGiore et al. |
| 2013/0109254 A1 | 5/2013 | Klardie et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 0158520 A1 | 8/2001 |
| WO | 02068042 A1 | 9/2002 |

(56) References Cited

FOREIGN PATENT DOCUMENTS

| WO | 2004045707 A1 | 6/2004 |
| WO | 2008018067 A2 | 2/2008 |
| WO | 2008053789 A1 | 5/2008 |
| WO | 2008/100841 A1 | 8/2008 |
| WO | 2009025816 A1 | 2/2009 |
| WO | 2009102536 A1 | 8/2009 |
| WO | 2013162775 A2 | 10/2013 |
| WO | 2014018092 A1 | 1/2014 |

* cited by examiner

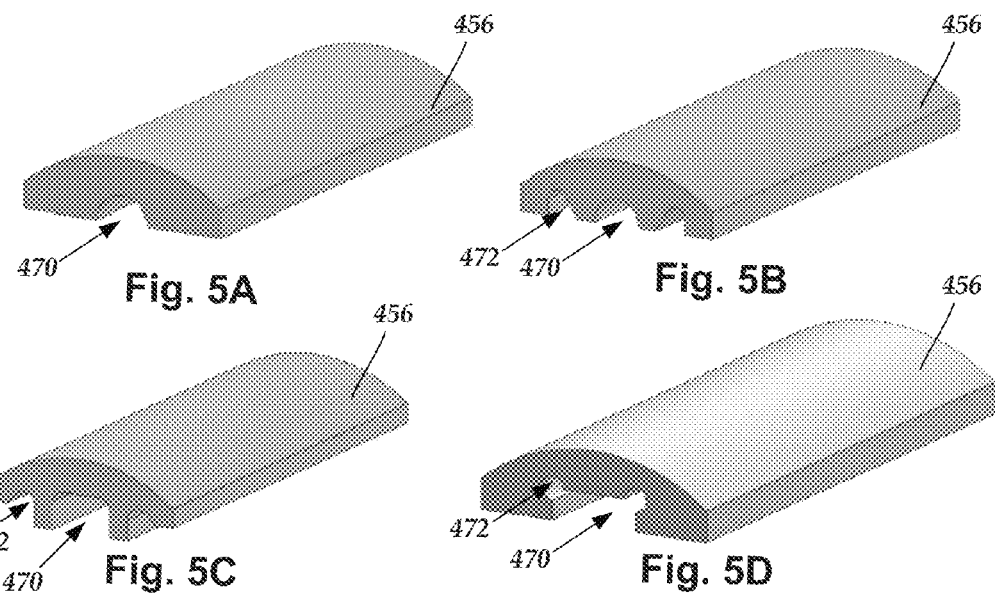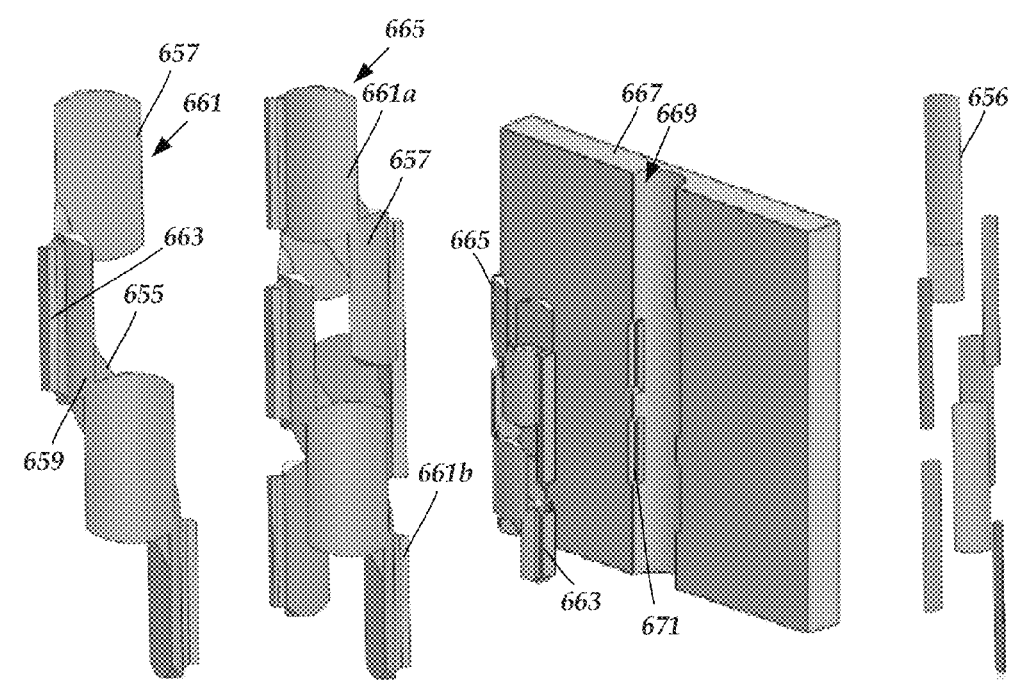

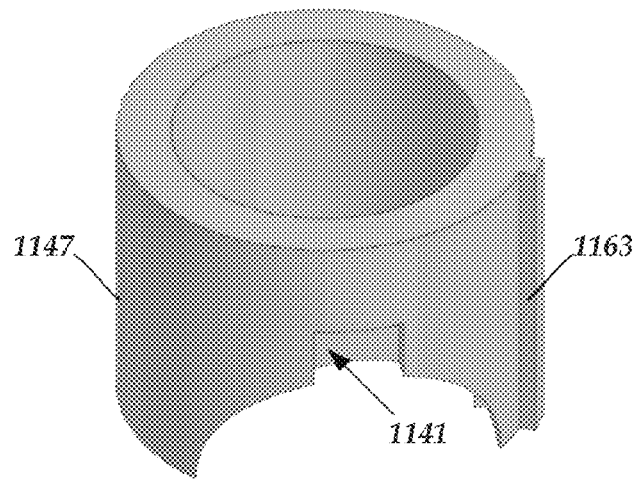
Fig. 12A
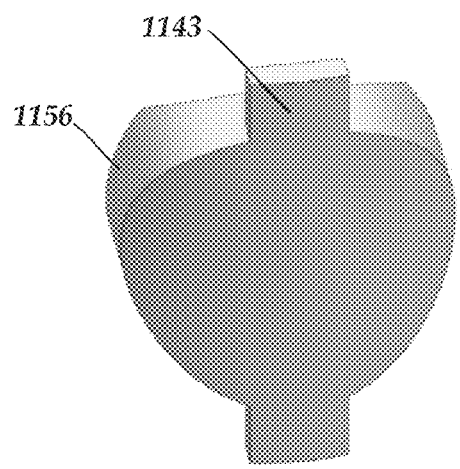 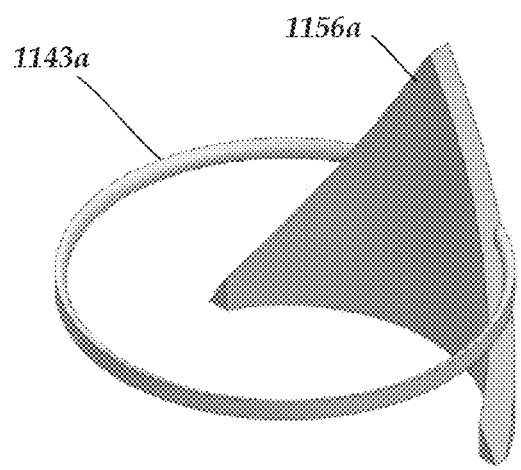
Fig. 12B  Fig. 12C

ELECTRICAL STIMULATION LEADS WITH HELICALLY ARRANGED ELECTRODES AND METHODS OF MAKING AND USING

CROSS-REFERENCE TO RELATED APPLICATIONS

This application claims the benefit under 35 U.S.C. §119 (e) of U.S. Provisional Patent Application Ser. No. 61/910,678, filed Dec. 2, 2013, which is incorporated herein by reference.

FIELD

The invention is directed to the area of electrical stimulation systems and methods of making and using the systems. The present invention is also directed to electrical stimulation leads with segmented electrodes that can be used for directed electrical stimulation, as well as methods of making and using the segmented electrodes, leads, and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

One embodiment is a stimulation lead including a lead body having a longitudinal length, a distal portion, and a proximal portion; terminals disposed along the proximal portion of the lead body; a non-conductive electrode carrier coupled to, or disposed along, the distal portion of the lead body and defining segmented electrode receiving openings arranged in a single helix or a double helix or other helical arrangement; segmented electrodes extending around no more than 75% of a circumference of the lead with each of the segmented electrodes disposed in a different one of the segmented electrode receiving openings of the electrode carrier; and conductors extending along the lead body and coupling the electrodes to the terminals.

Another embodiment is a method of making a stimulation lead. The method includes forming a rib framework with a plurality of pre-electrodes attached together in a single or a double helix or other helical arrangement; attaching a conductor to each of the pre-electrodes; disposing the rib framework into a mold and forming a lead body between the pre-electrodes; and removing a portion of the lead body and the pre-electrodes to generate separated segmented electrodes arranged in the single helix or the double helix.

Yet another embodiment is a method of making a stimulation lead. The method includes disposing segmented electrodes and conductors in a first mold; attaching each of the conductors to one of the segmented electrodes; molding a carrier over the segmented electrodes using the first mold; and rolling the carrier with the segmented electrodes into a cylinder. The segmented electrodes are arranged in the first mold so that when rolled into a cylinder with the carrier, the segmented electrodes are arranged in a single helix or a double helix or other helical arrangement. The method also includes placing the cylinder into a second mold; and molding a lead body between the segmented electrodes using the second mold.

A further embodiment is a method of making a stimulation lead. The method includes forming an electrode assembly by alternating segmented electrodes with non-conductive spacers shaped to receive the segmented electrodes. The segmented electrodes are positioned in the electrode assembly in a single helix or a double helix or other helical arrangement. The method further includes placing the electrode assembly into a mold; and molding a lead body between the segmented electrodes using the mold.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 5A is a schematic perspective view of one embodiment of a segmented electrode with a channel, according to the invention;

FIG. 5B is a schematic perspective view of one embodiment of a segmented electrode with multiple channels, according to the invention;

FIG. 5C is a schematic perspective view of another embodiment of a segmented electrode with multiple channels, according to the invention;

FIG. 5D is a schematic perspective view of yet another embodiment of a segmented electrode with multiple channels, according to the invention;

FIG. 6A is a schematic side view of one embodiment of a rib framework of pre-electrodes, according to the invention;

FIG. 6B is a schematic side view of a rib assembly formed using two rib frameworks of FIG. 6A, according to the invention;

FIG. 6C is a schematic perspective view of the rib assembly of FIG. 6B and a mold for receiving the assembly, according to the invention;

FIG. 6D is a schematic side view of segmented electrodes formed from the rib assembly of FIG. 6B with the lead body removed for clarity of illustration, according to the invention;

FIG. 12A is a schematic perspective view of one embodiment of a segmented electrode of the electrode assembly of FIG. 11A, according to the invention;

FIG. 12B is a schematic perspective view of one embodiment of a spacer of the electrode assembly of FIG. 11A, according to the invention;

FIG. 12C is a schematic perspective view of another embodiment of a segmented electrode for use in an electrode assembly, according to the invention;

DETAILED DESCRIPTION

The invention is directed to the area of electrical stimulation systems and methods of making and using the systems. The present invention is also directed to electrical stimulation leads with segmented electrodes that can be used for directed electrical stimulation, as well as methods of making and using the segmented electrodes, leads, and electrical stimulation systems.

A lead for deep brain stimulation can include stimulation electrodes, recording electrodes, or a combination of both. At least some of the stimulation electrodes, recording electrodes, or both are provided in the form of segmented electrodes that extend only partially around the circumference of the lead. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves and tissues.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and U.S. patent application Ser. Nos. 12/177,823; 13/667,953; and 13/750,725, all of which are incorporated by reference.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead can include both recording electrodes and stimulation electrodes or electrodes can be used for both recording and stimulation.

Figure 1:
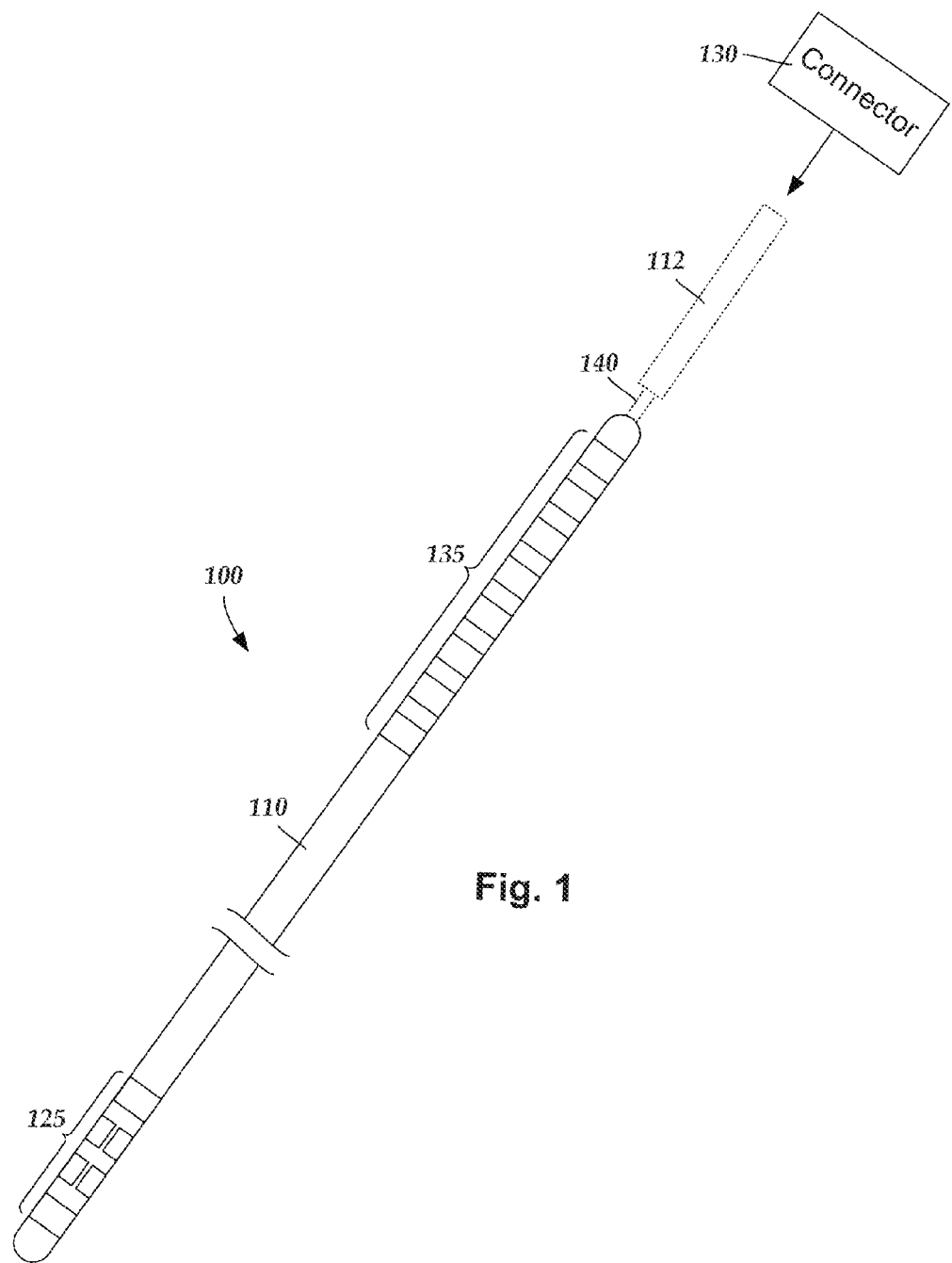
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 132 for connection of the electrodes to a control unit, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 112 to assist insertion into the lead 110, as well as rotation of the stylet 140 and lead 110. The connector 132 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator can have more or fewer than eight stimulation channels (e.g., 4-, 6-, 16-, 32-, or more stimulation channels). The control unit can have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician can observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes typically do not enable stimulus current to be directed from only a limited angular range around of the lead. Segmented electrodes, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

The lead 100 includes a lead body 110, one or more optional ring electrodes 120, and a plurality of segmented electrodes 130. The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Figure 3A:
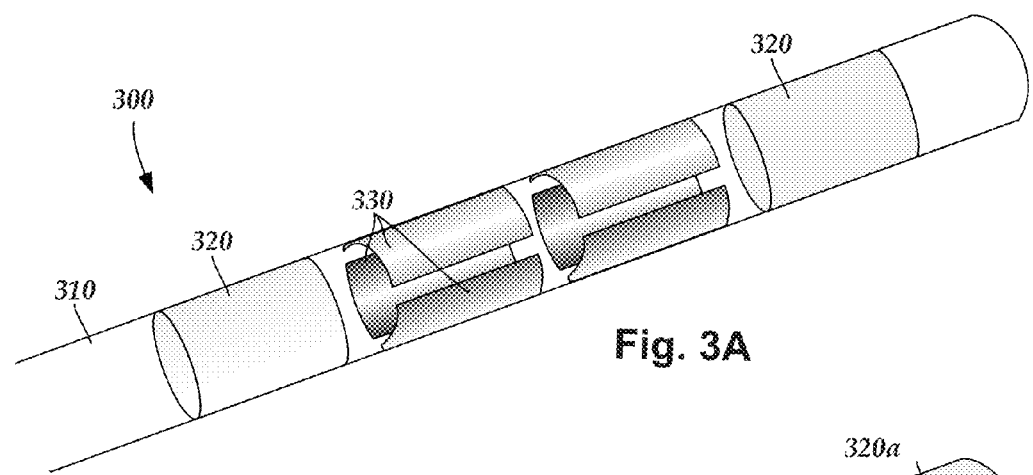
FIG. 3A is a perspective view of one embodiment of a portion of a lead having a plurality of segmented electrodes, according to the invention.
Figure 3B:
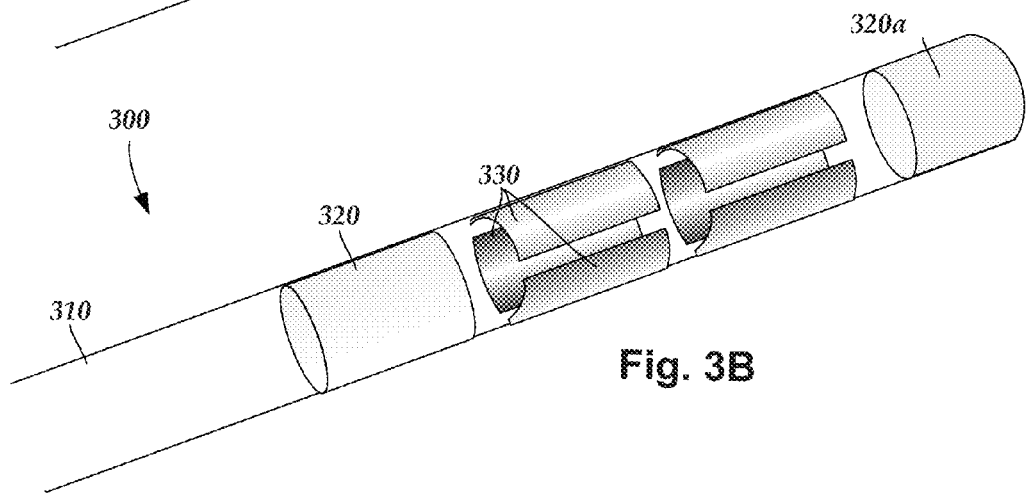
FIG. 3B is a perspective view of another embodiment of a portion of a lead having a plurality of segmented electrodes, according to the invention.

Stimulation electrodes in the form of ring electrodes 120 can be disposed on any part of the lead body 110, usually near a distal end of the lead 100. In FIG. 1, the lead 100 includes two ring electrodes 120. Any number of ring electrodes 120 can be disposed along the length of the lead body 110 including, for example, one, two three, four, five, six, seven, eight, nine, ten, eleven, twelve, thirteen, fourteen, fifteen, sixteen or more ring electrodes 120. It will be understood that any number of ring electrodes can be disposed along the length of the lead body 110. In some embodiments, the ring electrodes 120 are substantially cylindrical and wrap around the entire circumference of the lead body 110. In some embodiments, the outer diameters of the ring electrodes 120 are substantially equal to the outer diameter of the lead body 110. The length of the ring electrodes 120 may vary according to the desired treatment and the location of the target neurons. In some embodiments the length of the ring electrodes 120 are less than or equal to the diameters of the ring electrodes 120. In other embodiments, the lengths of the ring electrodes 120 are greater than the diameters of the ring electrodes 120. The distal-most ring electrode 120 may be a tip electrode (see, e.g., tip electrode 320a of FIG. 3E) which covers most, or all, of the distal tip of the lead.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Patent Application Publication Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321, all of which are incorporated herein by reference.

The lead 100 is shown having a plurality of segmented electrodes 130. Any number of segmented electrodes 130 may be disposed on the lead body 110 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 110. A segmented electrode 130 typically extends only 75%, 67%, 60%, 50%, 40%, 33%, 25%, 20%, 17%, 15%, or less around the circumference of the lead.

The segmented electrodes 130 may vary in size and shape. In some embodiments, the segmented electrodes 130 are all of the same size, shape, diameter, width or area or any combination thereof. For example, in some embodiments, the segmented electrodes all have a uniform surface area (for example, 1.5 mm$^2$). As will be described below, the segmented electrodes can be arranged in a single or double helix or any other helical arrangement.

The spacing between neighboring electrodes may be the same or different. In at least some embodiments, equal spaces, gaps or cutouts are disposed between each segmented electrode 130. In other embodiments, the spaces, gaps or cutouts between the segmented electrodes 130 may differ in size or shape.

Conductor wires that attach to the ring electrodes 120 or segmented electrodes 130 extend along the lead body 110. These conductor wires may extend through the material of the lead 100 or along one or more lumens defined by the lead 100, or both. The conductor wires are presented at a connector (via terminals) for coupling of the electrodes 120, 130 to a control unit (not shown).

When the lead 100 includes both ring electrodes 120 and segmented electrodes 130, the ring electrodes 120 and the segmented electrodes 130 may be arranged in any suitable configuration. For example, when the lead 100 includes two ring electrodes 120 and segmented electrodes 130, the ring electrodes 120 can flank the segmented electrodes 130 (see e.g., FIGS. 1 and 3A). Alternately, the ring electrodes 120 can be disposed proximal to the segmented electrodes 130 or the ring electrodes 120 can be disposed distal to the segmented electrodes 130 or any other suitable arrangement. One of the ring electrodes can be a tip electrode (see, tip electrode 320a of FIG. 3G). It will be understood that other configurations are possible as well (e.g., alternating ring and segmented electrodes, or the like). By varying the location of the segmented electrodes 130, different coverage of the target neurons may be selected.

Figure 2:
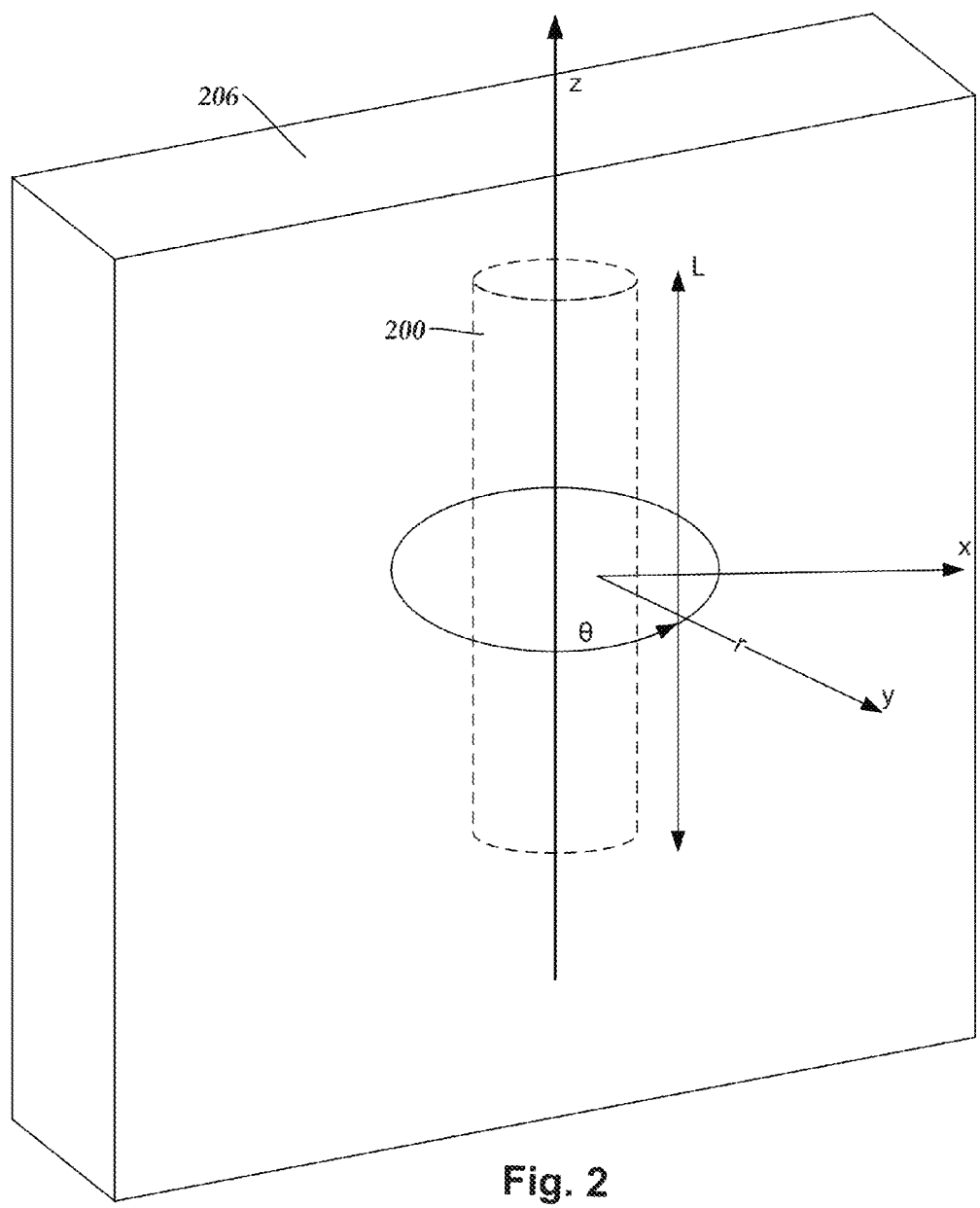
FIG. 2 is a schematic diagram of radial current steering along various electrode levels along the length of a lead, according to the invention.

FIG. 2 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 2, the centroid of stimulation can be shifted at each level along the length of the lead 200. The use of multiple segmented electrodes at different levels along the length of the lead allows for three-dimensional current steering. In some embodiments, the segmented electrodes are shifted collectively (i.e., the centroid of simulation is similar at each level along the length of the lead). In at least some other embodiments, each segmented electrode is controlled independently. It will be understood that different stimulation profiles may be produced by varying the number of segmented electrodes at each level.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

Segmented electrodes can be used to tailor the stimulation region so that, instead of stimulating tissue around the circumference of the lead as would be achieved using a ring electrode, the stimulation region can be directionally targeted. In some instances, it is desirable to target a parallelepiped (or slab) region 206 that contains the electrodes of the lead 200, as illustrated in FIG. 2. One arrangement for directing a stimulation field into a parallelepiped region uses segmented electrodes disposed on opposite sides of a lead.

One challenge to making leads with segmented electrodes is the correct placement of the electrodes, and retention of the desired electrode placement, during the manufacturing process. This can be particularly challenging when the electrodes are to be arranged in a single or double helix or other helical arrangement. An electrode carrier can be utilized to hold the electrodes in the desired single or double helix arrangement during the manufacture of the lead. The electrode carrier is made of a non-conductive material to electrically isolate the segmented electrodes from each other and include openings to receive the segmented electrodes. The openings are arranged in a single or double helix.

Figure 4A:
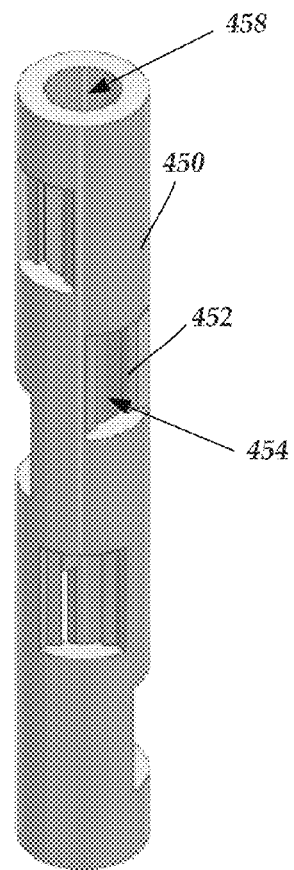
FIG. 4A is a schematic perspective view of one embodiment of an electrode carrier, according to the invention.

FIG. 4A illustrates one embodiment of an electrode carrier 450. The electrode carrier 450 defines segmented electrode receiving openings 454 which can be arranged in a single or double helix or any other helical arrangement. The segmented electrode receiving openings 454 are arranged to receive the segmented electrodes 456 (see, for example, FIG. 4B). The electrode carrier 450 also has a central lumen 458 through which conductors 460 (see, FIGS. 4B and 4C) attached to the segmented electrodes can pass on the way to the remainder of the lead. The central lumen 458 may be open at both ends of the electrode carrier 450 or may be closed at the distal end of the electrode carrier. It will be recognized that ring electrodes can be incorporated in a lead distal or proximal to the electrode carrier 450 and that a tip electrode can be incorporated in a lead distal to the electrode carrier.

The electrode carrier 450 is formed of a non-conductive material which may be the same material as the lead body, for example, silicone, polyurethane (e.g., TECOTHANE™ or ISOPLAST™), polyetheretherketone, other rigid plastics or any other suitable biocompatible material. In some embodiments, the electrode carrier 450 may be made of a material that is stiffer or harder than the material of the lead body. For example, the material of the electrode carrier 450 may have a higher durometer than that of the lead body. In some embodiments, the electrode carrier 450 is made of the same type of polymer material (e.g., polyurethane or silicone) as the lead body, but with a higher durometer than the lead body. A stiffer or harder material for the electrode carrier may facilitate manufacturing. The electrode carrier can be made by any suitable manufacturing method including, but not limited to, molding, casting, laser cutting, chemical etching, or 3D printing. Additional examples of materials, manufacturing methods, and designs for electrode carriers can be found in U.S. patent application Ser. No. 13/951,057, incorporated herein by reference.

Figure 4B:
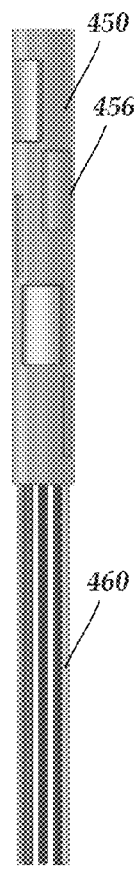
FIG. 4B is a schematic side view of one embodiment of the electrode carrier of FIG. 4A with segmented electrodes and associated conductors, according to the invention.
Figure 4C:
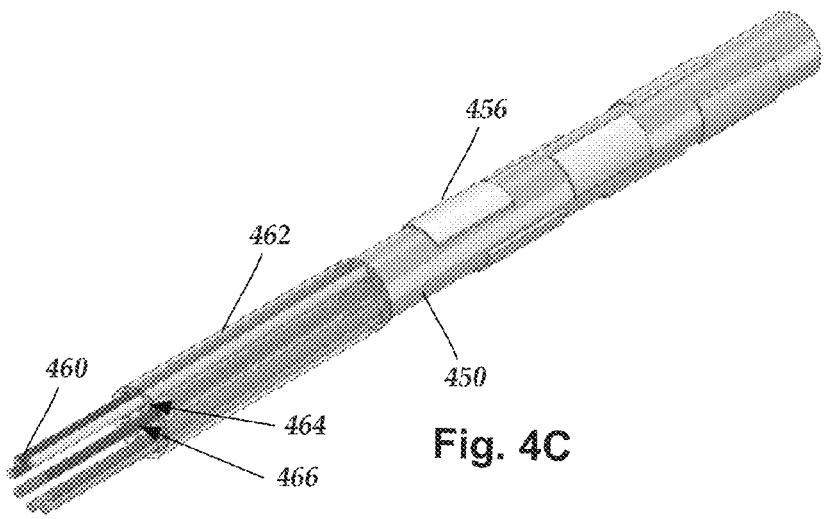
FIG. 4C is a schematic perspective view of one embodiment of the electrode carrier of FIG. 4A with segmented electrodes, associated conductors, and a multi-lumen tube, according to the invention.

FIG. 4B illustrates the segmented electrodes 456 inserted into the electrode receiving openings 454. Optionally, the electrode carrier 450 includes steps 452 (see, FIG. 4A) in the electrode receiving openings 454 to locate and set electrode depth in the carrier. In some embodiments, the segmented electrodes 456 protrude radially out of the electrode receiving openings 454, as illustrated in FIG. 4C. in some embodiments, the segmented electrodes 456 form a friction fit with, or snap into, the electrode receiving openings 454 of the electrode carrier 450. In other embodiments, the segmented electrodes 456 may be held within the openings 454 merely by applying tension to conductors 460 attached to the segmented electrodes. In some embodiments, adhesive or other fastening mechanisms may be used to hold the segmented electrodes in place once positioned.

In some embodiments, a non-conductive multi-lumen tube 462 can be positioned near or adjacent the proximal end of the electrode carrier 450, as illustrated in FIG. 4C. The multi-lumen tube 462 includes a set of conductor lumens 464 arranged concentrically around a central lumen 466. Each conductor lumen 464 receives one or more of the conductors 460. The central lumen 466 may be configured and arranged to receive a stylet during implantation of the lead or for delivery of fluids to the stimulation site. In some embodiments, the multi-lumen tube 462 is attached to the electrode carrier 450 by, for example, adhesive, polymeric reflow, or the like. The multi-lumen tube can be made of any suitable biocompatible material including, but not limited to, polyurethane, silicone, polyetheretherketone, or the like.

In at least some embodiments, a conductor 460 can be attached to a segmented electrode 456 prior to placement of the segmented electrode in the electrode carrier 450. The conductor 460 can be fed through the corresponding segmented electrode receiving opening 454, down the lumen 458, and through a conductor lumen 464 of the multi-lumen tube 462. Alternatively, the conductor 460 can be threaded through the multi-lumen tube 462 and electrode carrier 450 prior to attachment to the segmented electrode 456.

In some embodiments, an over tube (e.g. a silicone tube) may be placed over the electrode carrier 450 then the over tube can be backfilled with epoxy, silicone, polyurethane, or other polymeric material to form an outer lead body (not shown) between the segmented electrodes 456 and optionally over the multi-lumen tube 462 (or a portion thereof). The backfill material may also completely or partially fill the central lumen 458 of the electrode carrier 450. The over tube can then be removed and any excess backfill material can be removed (by, for example, grinding, cutting, trimming, ablating, or the like) to leave a stimulation surface of the segmented electrodes 456 exposed.

FIGS. 5A-5D illustrate different embodiments of the segmented electrode 456. The segmented electrode 456 can include a channel 470 for receiving and attachment (by, for example, welding, soldering, crimping, adhesive, or the like) of a conductor 460 (see, FIGS. 4B and 4C). The segmented electrode 456 may include one or more additional channels 472. The channel 470 or additional channels 472 (or any combination thereof) may be sized or shaped to fit partially around or attach to one or more of the steps 452 (see, FIG. 4A) to facilitate positioning of the segmented electrode 456 in the electrode carrier 450. Alternatively or additionally, polymer may be flowed into the channel 470 or additional channels 472 (or any combination thereof) after placement of the segmented electrode 456 in the electrode carrier 450 to lock the segmented electrode within the electrode carrier. FIG. 5A illustrates a segmented electrode 456 with a single channel 470. FIG. 5B illustrates a segmented electrode 456 with a channel 470 flanked by two additional channels 472 that are spaced apart from side edges of the segmented electrode. FIG. 5C illustrates a segmented electrode 456 with a channel 470 flanked by two additional channels 472 that are extend to, and are open at, the side edges of the segmented electrode. FIG. 5D illustrates a segmented electrode 456 with a channel 470 with two additional channels 472 that open into channel 470. The channel 470 or additional channels 472 can be added to any of the other segmented electrodes described herein.

FIGS. 6A-6D illustrate steps in another method of forming a lead with segmented electrodes arranged in a single helix, double helix, or other helical arrangement. A set of pre-electrodes 657 are attached together at corners 659 of the pre-electrodes to form a rib framework 661. Optionally, additional connecting material 655 can be provided to couple together the pre-electrode 657. One or more of the pre-electrodes 657 includes an alignment tab 663. In the illustrated example of FIG. 6A, the rib framework 661 includes four pre-electrodes 657 arranged in a single helix with an alignment tab 663 on each of the second and fourth pre-electrodes counting from the top of the framework. The pre-electrodes 657, alignment tabs 663, and optional connecting material 655 are typically formed of the metallic material of the final segmented electrodes. The entire rib framework 661 can be formed by any suitable methods including, but not limited to, molding, sintering, die casting, cutting and shaping, and the like.

FIG. 6B illustrates two rib frameworks 661a, 661b formed into a single rib assembly 665 with a double helix of pre-electrodes 657. The two rib frameworks 661 are optionally attached to each other. Conductors (not shown for clarity of illustration) are individually attached to the pre-electrodes by, for example, welding, soldering, adhesive, or the like.

The rib assembly 665 with attached conductors (not shown) is inserted into a channel 669 in a mold 667, as illustrated in FIG. 6C. Only one half of the mold 667 is shown in FIG. 6C and it will be understood that the other half fits over the illustrated half and includes a similar channel. The channel 669 includes slots 671 which receive the alignment tabs 663 of the rib assembly 665. The alignment tabs 663 and slots 671 orient the rib assembly 665 within the channel 669 and maintain that orientation during the molding process.

After placement of the rib assembly 665 in the mold 667, the mold is closed and a non-conductive lead body material is introduced into the channel to form a portion of a lead body (see, lead body 110 of FIG. 1) around the rib assembly 665. The lead body and rib assembly 665 are removed from the mold and then portions of the lead body and rib assembly (including at least the alignment tabs, corners, and optional connective material) are removed to separate the pre-electrodes 657 (see, FIG. 6A) into the segmented electrodes 656, as illustrated in FIG. 6D (for clarity of illustration, the lead body is not shown in FIG. 6D so that the arrangement of the segmented electrodes can be viewed.) The removal of portions of the lead body and rib assembly can be accomplished by any suitable method including, but not limited to, grinding (for example, centerless grinding), etching, ablation, and the like. The pre-electrodes 657 can have a thickness that is greater (or have a portion that extends further radially inward) for the portion of the pre-electrode that will form the segmented electrode 656 and thinner (or disposed further radially outward) at the corners 659 and optional connecting material 655 so that the removal step leaves the desired segmented electrode.

Figures 7A, 7B, 7C, 7D:
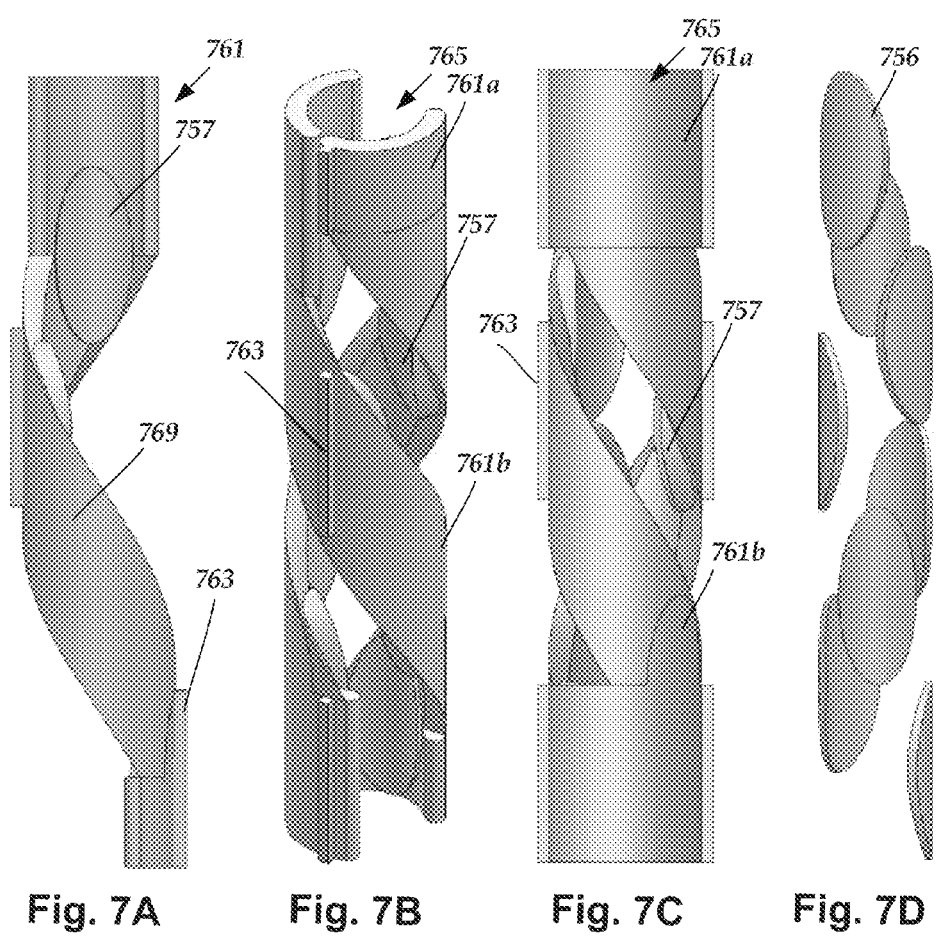
FIG. 7A is a schematic side view of one embodiment of a rib framework of pre-electrodes on a ribbon, according to the invention.
FIG. 7B is a schematic perspective view of a rib assembly formed using two rib frameworks of FIG. 7A, according to the invention.
FIG. 7C is a schematic side view of the rib assembly of FIG. 7B, according to the invention.
FIG. 7D is a schematic side view of segmented electrodes formed from the rib assembly of FIG. 7B with the lead body removed for clarity of illustration, according to the invention.

FIGS. 7A-7D illustrate an alternative arrangement of pre-electrodes formed in a rib framework. A set of pre-electrodes 757 are attached to an inner surface of a ribbon 769 to form a rib framework 761, as illustrated in FIG. 7A. One or more alignment tabs 763 are also attached to an outer surface of the ribbon 769. In some embodiments, the pre-electrodes 757, alignment tabs 763, or both are formed integrally with ribbon 769 and made of the same conductive material. In other embodiments, the pre-electrodes 757, alignment tabs 763, or both are mechanically attached to the ribbon 769 by, for example, welding, soldering, adhesive, or the like and may be made of the same or different materials compared to the ribbon. In the illustrated example of FIG. 7A, the rib framework 761 includes four pre-electrodes 757 arranged in a single helix with two alignment tabs 763 located opposite the second and fourth pre-electrodes counting from the top of the framework.

FIG. 7B illustrates two rib frameworks 761a, 761b formed into a single rib assembly 765 with a double helix of pre-electrodes 757. The two rib frameworks 761 are optionally attached to each other. Conductors (not shown for clarity of illustration) are individually attached to the pre-electrodes by, for example, welding, soldering, adhesive, or the like. FIG. 7C is another view of the rib assembly 765 with the alignment tabs 763 arranged on the right and left sides of the rib assembly in the view.

Similar to the embodiment of FIGS. 6A-6D, the rib assembly 765 with attached conductors (not shown) is inserted into a channel (not shown) in a mold (not shown). The channel includes slots which receive the alignment tabs 763 of the rib assembly 765. The alignment tabs 763 and slots orient the rib assembly 765 within the channel and maintain that orientation during the molding process.

After placement of the rib assembly 765 in the mold, the mold is closed and a non-conductive lead body material is introduced into the channel to form a portion of a lead body around the rib assembly 765. The lead body and rib assembly 765 are removed from the mold and then portions of the lead body and rib assembly (including at least the alignment tabs 763 and ribbon 769) are removed to separate the pre-electrodes 757 (see, FIG. 7A) into the segmented electrodes 756, as illustrated in FIG. 7D (for clarity of illustration, the lead body is not shown in FIG. 7D so that the arrangement of the segmented electrodes can be viewed.) The removal of portions of the lead body and rib assembly can be accomplished by any suitable method including, but not limited to, grinding (for example, centerless grinding), etching, ablation, and the like.

Figures 8A, 8B, 8C:
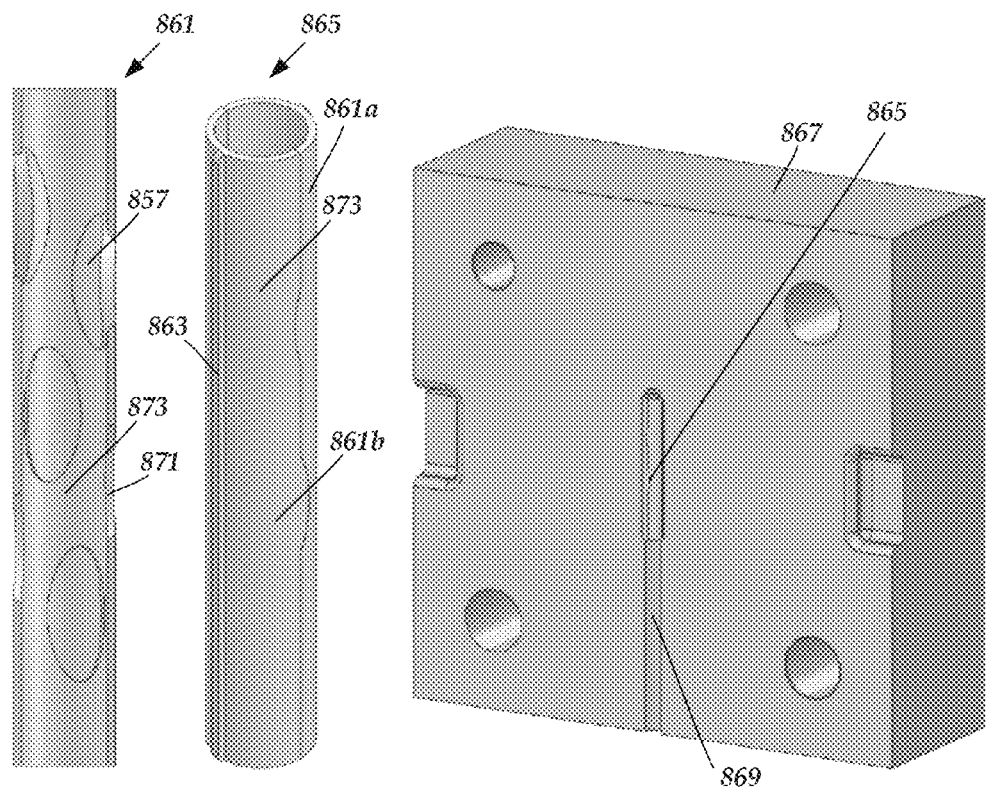
FIG. 8A is a schematic side view of one embodiment of a rib framework of pre-electrodes in a half-cylinder, according to the invention.
FIG. 8B is a schematic side view of a rib assembly formed using two rib frameworks of FIG. 8A, according to the invention.
FIG. 8C is a schematic perspective view of the rib assembly of FIG. 8B and a mold for receiving the assembly, according to the invention.

FIGS. 8A-8C illustrate another arrangement of pre-electrodes formed in a rib framework. A set of pre-electrodes 857 are formed in a half-cylinder 873 to produce a rib framework 861, as illustrated in FIG. 8A. The pre-electrodes 857 are thicker than adjacent portions of the half-cylinder 873 and extend further into the interior of the half-cylinder, as illustrated in FIG. 8A. The half-cylinder 873 may include divots 871 that receive the curved portion of a pre-electrode from an opposing half-cylinder (see, FIG. 8B).

As illustrated in FIG. 8B, one or more alignment tabs 863 are attached to the half-cylinder 873. In some embodiments, the pre-electrodes 857, alignment tabs 863, or both are formed integrally with the half-cylinder 873 and made of the same conductive material. In other embodiments, the pre-electrodes 857, alignment tabs 863, or both are mechanically attached to the half-cylinder 873 by, for example, welding, soldering, adhesive, or the like and may be made of the same or different materials compared to the other portions of the half-cylinder. In the illustrated example of FIGS. 8A and 8B, the rib framework 861 includes four pre-electrodes 857 arranged in a single helix with an alignment tab 863 extending along the length of the rib framework 861.

FIG. 8B illustrates two rib frameworks 861a, 861b forming a cylinder of a single rib assembly 865 with a double helix of pre-electrodes 857. The two rib frameworks 861 are attached to each other. In some embodiments, this attachment may be by friction fit, adhesive, welding, soldering, or any suitable mechanism. Conductors (not shown for clarity of illustration) are individually attached to the pre-electrodes by, for example, welding, soldering, adhesive, or the like.

The rib assembly 865 with attached conductors (not shown) is inserted into a channel 869 in a mold 867, as illustrated in FIG. 8C. Only one half of the mold 867 is shown in FIG. 8C and it will be understood that the other half fits over the illustrated half and includes a similar channel. The channel 869 includes slots (not shown) which receive the alignment tabs 863 (see, FIG. 8B) of the rib assembly 865. The alignment tabs and slots orient the rib assembly 865 within the channel 869 and maintain that orientation during the molding process.

After placement of the rib assembly 865 in the mold 867, the mold is closed and a non-conductive lead material is introduced into the channel to form a lead body (see, lead body 110 of FIG. 1) around the rib assembly 865. The lead body and rib assembly 865 are removed from the mold and then portions of the lead body and rib assembly (including at least the alignment tabs 863 and material of the half-cylinder 873 between the pre-electrodes 857) are removed to separate the pre-electrodes 857 (see, FIG. 8A) into the segmented electrodes (which can appear similar to segmented electrodes 756, as illustrated in FIG. 7D.) The removal of portions of the lead body and rib assembly can be accomplished by any suitable method including, but not limited to, grinding (for example, centerless grinding), etching, ablation, and the like.

Figures 9A, 9B, 9C:
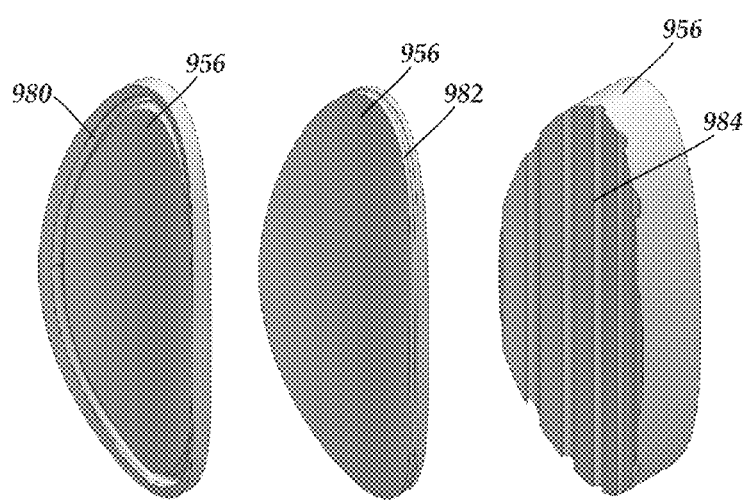
FIG. 9A is a schematic perspective view of one embodiment of a segmented electrode with a circumferential channel, according to the invention.
FIG. 9B is a schematic perspective view of one embodiment of a segmented electrode with a stepped edge, according to the invention.
FIG. 9C is a schematic perspective view of one embodiment of a segmented electrode with multiple longitudinal channels, according to the invention.

FIGS. 9A-9C illustrate different embodiments of the segmented electrode 956. These segmented electrodes may be used, for example, in the embodiments described with respect to FIGS. 6A-6D, 7A-7D, and 8A-8D. The segmented electrode can include, for example, one or more circumferential channels 980 as illustrated in FIG. 9A or one or more longitudinal channels 994 as illustrated in FIG. 9C. The segmented electrode 456 may a stepped edge 982 as illustrated in FIG. 9B. Molding material (e.g., epoxy, silicon, polyurethane, or the like) may be flowed into the circumferential channel(s) 980 or longitudinal channel(s) 984 or around the stepped edge 982 to facilitate holding the segmented electrode within the lead body after molding. The circumferential channel 980, longitudinal channel 984, or stepped edge 982 can be added to any of the other electrodes described herein.

Figure 10A:
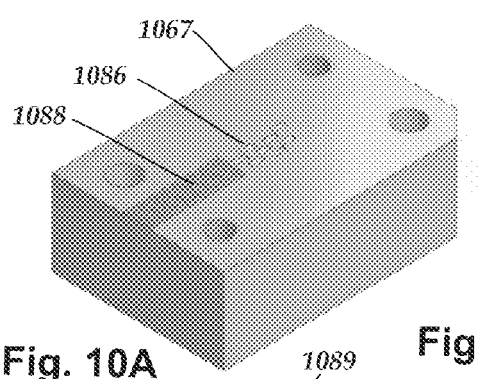
FIG. 10A is a schematic perspective view of one embodiment of a mold for receiving segmented electrodes and conductors, according to the invention.

FIGS. 10A-10G illustrate another method of forming a lead with electrodes arranged in a single or double helix or in any other helical pattern. FIG. 10A illustrates a bottom portion of a mold 1067 that has electrode cavities 1086 for placement of the segmented electrodes and conductor cavities 1088 for placement of the conductors. The segmented electrodes 1056 (see, FIG. 10C) are placed in the electrode cavities 1086, a portion of each of the conductors 1060 is placed in the conductor cavities 1088, and each conductor is attached to a corresponding segmented electrode. The mold is then closed with a top portion and molding material is introduced around at least the segmented electrodes. Examples of suitable molding materials include any flexible, biocompatible, non-conductive polymer material includes, but not limited to, silicone, polyurethane, or the like.

Figure 10B:
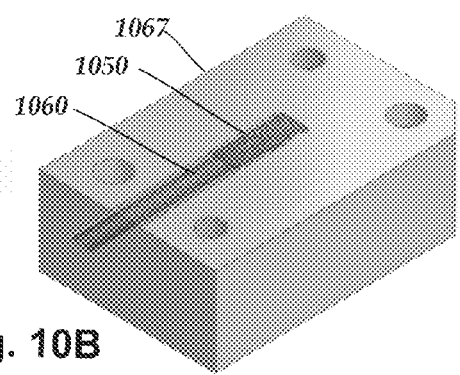
FIG. 10B is a schematic perspective view of the mold of FIG. 10A with a molded carrier, the segmented electrodes, and conductors, according to the invention.
Figure 10C:
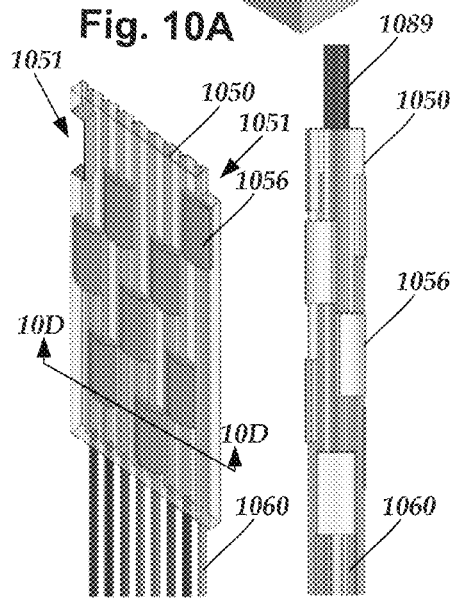
FIG. 10C is a schematic perspective view of one embodiment of a molded carrier with segmented electrodes and conductors, according to the invention.

FIG. 10B illustrates the result of the molding procedure with mold 1067. A molded carrier 1050 is formed from the molding material around the segmented electrodes. FIG. 10C illustrates the molded carrier 1050, segmented electrodes 1056, and conductors removed from the mold. The molded carrier 1050 may include indentations 1051 or tabs that can be matched when the carrier is rolled up as described below.

Figure 10E:
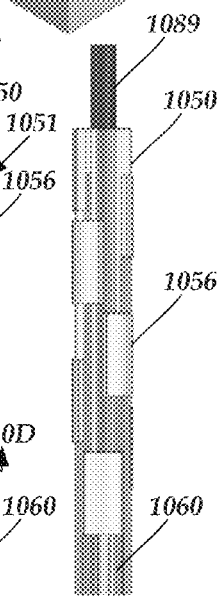
FIG. 10E is a schematic side view of the molded carrier, segmented electrodes, and conductors of FIG. 10C rolled into a cylinder, according to the invention.
Figure 10G:
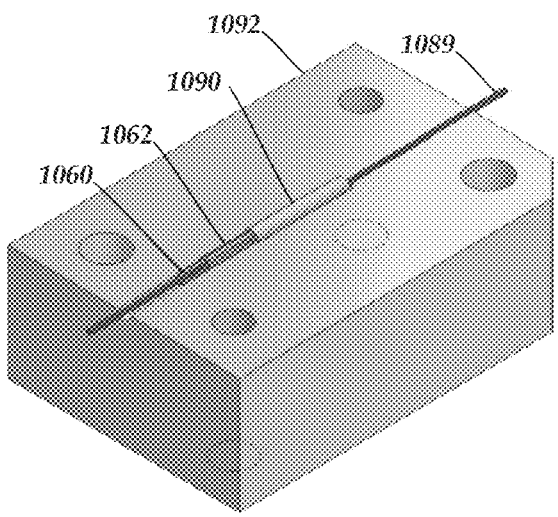
FIG. 10G is a schematic perspective view of the arrangement of FIG. 10F disposed in a mold, according to the invention.
Figure 10D:
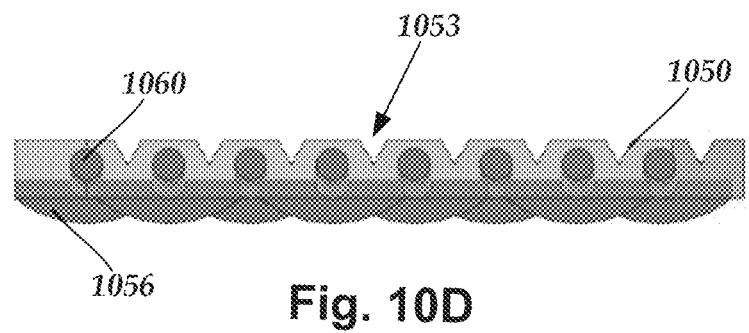
FIG. 10D is a schematic cross-sectional view of the molded carrier, segmented electrodes, and conductors of FIG. 10C, according to the invention.

In some embodiments, the molded carrier 1050 can include longitudinal notches 1053 formed in the surface of the carrier opposite the segmented electrodes 1056, as illustrated in FIG. 10D. The notches 1053 preferably extend the entire length of the carrier 1050 and are preferably parallel to the conductors 1060. These notches 1053 can be formed using an appropriately shaped mold 1067 or can be added after molding by ablation, cutting, or the like. The notches can have any suitable shape including, but not limited to, triangular, hemispherical, rectangular, or the like. The notches 1053 may facilitate rolling of the carrier 1050 into a cylinder as describe below. In at least some embodiments, the notches 1053 can be placed in an alternative arrangement with the conductors 1060, as illustrated in FIG. 10D.

Figure 10F:
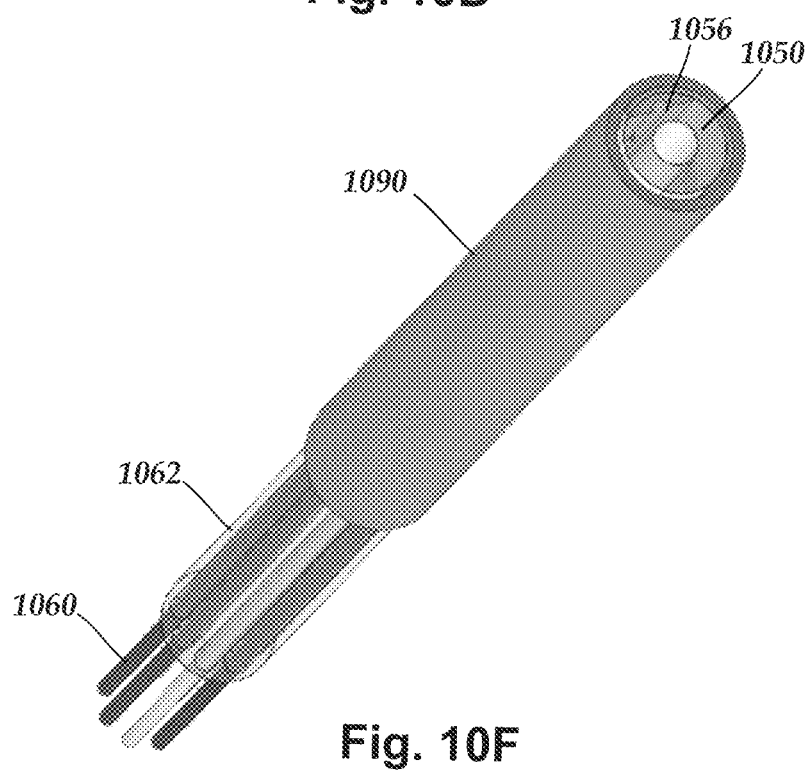
FIG. 10F is a schematic side view of the cylindrical molded carrier, segmented electrodes, and conductors of FIG. 10D with an over tube and multi-lumen tube, according to the invention.

The carrier 1050 is rolled into a cylinder with the segmented electrodes 1056 disposed on the outside of the cylinder, as illustrated in FIG. 10E. In at least some embodiments, the carrier 1050 is rolled around a mandrel 1089. In at least some embodiments, a multi-lumen tube 1062 is positioned adjacent the carrier with the conductors 1060 disposed within the lumens of the multi-lumen tube, as illustrated in FIG. 10F. The multi-lumen tube 1062 can be similar to the multi-lumen tube 462 illustrated in FIG. 4C and discussed above. In addition, an over tube 1090 can be placed over the carrier 1050 and segmented electrodes 1056, as illustrated in FIG. 10F. The over tube 1090 is temporary and is preferably easily removed. For example, the over tube 1090 may be formed of silicone.

Once the carrier 1050 (see, FIG. 10E) rolled into a cylinder with the over tube 1090 positioned over the carrier and segmented electrodes 1056, the arrangement is disposed in a channel of a second mold 1092, as illustrated in FIG. 10G (only the bottom portion of the second mold is illustrated, but the top portion can be similar.) The second mold 1092 is closed and a molding material such as, for example, epoxy, silicone, polyurethane, or the like, is introduced around the carrier, multi-lumen tube 1062, and conductors 1060 to form a lead body. Optionally, the mandrel 1089 remains with the arrangement. If not, the molding material may also flow into the lumen resulting from the removal of the mandrel. The arrangement is removed from the second mold 1092 and the over tube 1090 is removed to expose the stimulation surfaces of the segmented electrodes. In some embodiments, a portion of the lead body and segmented electrodes might be removed by grinding, trimming, cutting, or any other suitable method to expose the stimulation surfaces of the segmented electrodes.

Figures 11A, 11B, 11C:
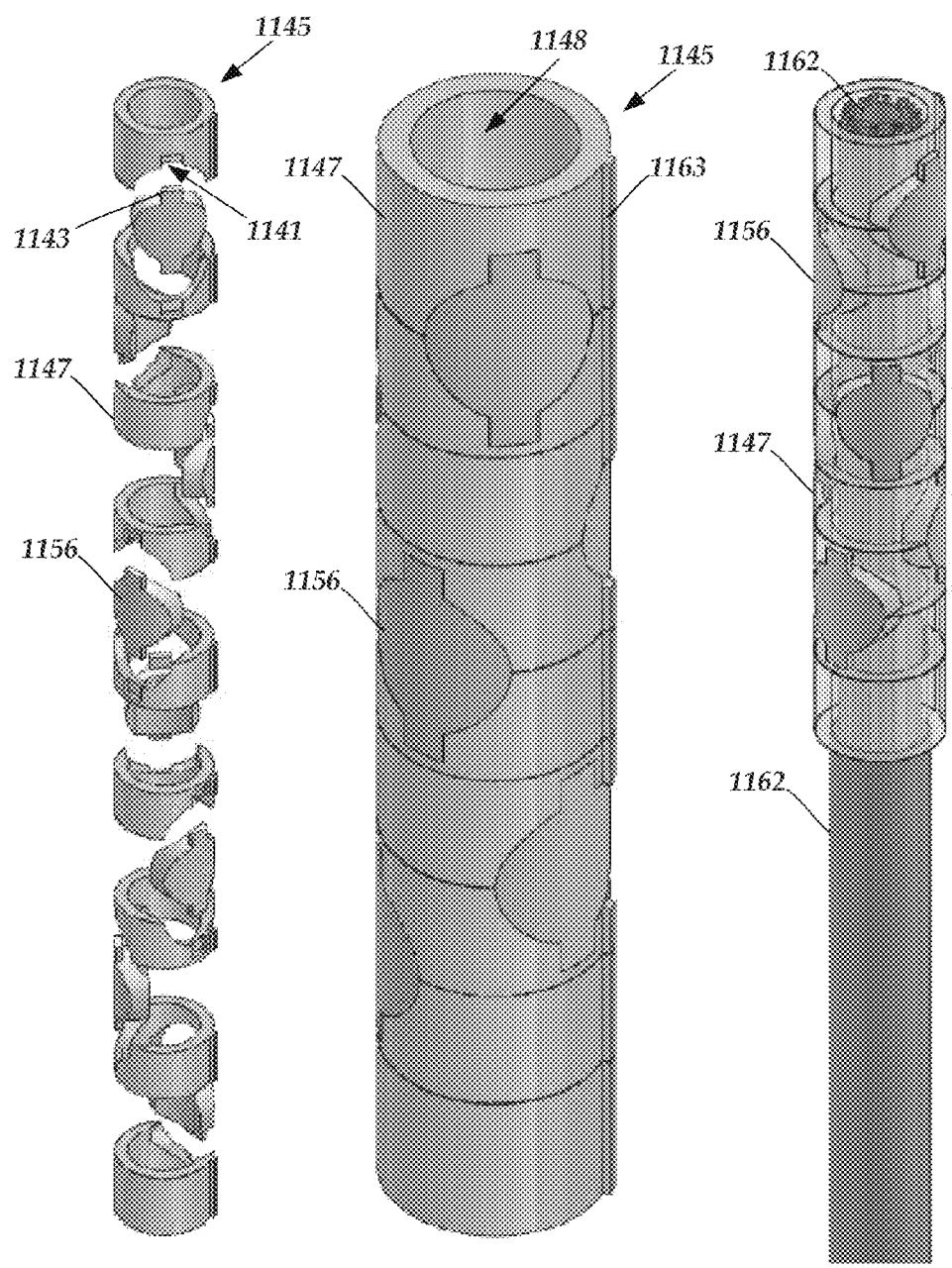
FIG. 11A is a schematic exploded perspective view of an electrode assembly of segmented electrodes and spacers, according to the invention.
FIG. 11B is a schematic perspective view of the electrode assembly of FIG. 11A, according to the invention.
FIG. 11C is a schematic perspective view of the electrode assembly of FIG. 11B with a multi-lumen tube, according to the invention.

FIGS. 11A-11C illustrate another method of forming a lead with electrodes arranged in a single or double helix or in any other helical pattern. In this arrangement, an electrode assembly 1145 is formed from alternating segmented electrodes 1156 and non-conducting spacers 1147, as illustrated in FIGS. 11A and 11B. The spacers 1147 locate and align the segmented electrodes 1156. In at least some embodiments, the spacers 1147 are each unique. In the illustrated embodiment of FIG. 11A, there are eight electrodes 1156 arranged in a double helix with nine unique spacers 1147. Optionally, one or more (or each) of the spacers 1147 include an aligning rib 1163 that aids in assembling the spacers and segmented electrodes 1156 in the correct orientation with the aligning ribs of the spacers aligned with each other, as illustrated in FIG. 11B.

In at least some embodiments, each segmented electrode 1156 has one or more alignment tabs 1143 and each of the spacers 1147 has one or more notches 1141. The notches 1141 each receive an alignment tab 1143 of one of the segmented electrodes. In some embodiments, the alignment tabs 1143 have a frictional fit with the notches 1141 or adhesive is used to hold the alignment tabs in the notches. It will be understood that in other embodiments, the alignment tabs may be positioned on the spacers with the notches on the segmented electrodes. In some embodiments, the alignment tabs 1143 are thinner than the segmented electrodes 1156 and positioned radially at the outer surface of the segmented electrodes. In such embodiments, the alignment tabs 1143 may be removed during manufacture by grinding down the segmented electrodes and lead body as described below.

One example of a spacer 1147 is provided in FIG. 12A. One example of a segmented electrode 1156 is provided in FIG. 12B. An alternative segmented electrode 1156a is illustrated in FIG. 12C and includes an alignment ring 1143a instead of an alignment tab.

Conductors (not shown) are attached to each of the segmented electrodes prior to or during formation of the electrode assembly 1145. The conductors extend through the central lumen 1148 of the electrode assembly 1145. The segmented electrodes 1156 and spacers 1147 may be coupled together by a friction fit or an adhesive may be used to hold the assembly 1145 together or the assembly 1145 may be built up around a mandrel (not shown) or any combination of these methods. In some embodiments, a multi-lumen tube 1162 (which is similar to the multi-lumen tube 462 illustrated in FIG. 4C) is positioned adjacent to or near the electrode assembly 1145, as illustrated in FIG. 11C. In some embodiments, the multi-lumen tube 1162 can extend into the lumen 1148 of the electrode assembly 1145, as illustrated in FIG. 11C. The outer part of the portion of the multi-lumen tube 1162 residing in the lumen 1148 may be removed (e.g., ablated) to facilitate coupling of the conductors extending along the multi-lumen tube to the segmented electrodes 1156.

The electrode assembly 1145 is disposed in a channel of a mold and a molding material such as, for example, epoxy, silicone, polyurethane, or the like, is introduced around the electrode assembly 1145, multi-lumen tube 1162, and conductors (not shown) to form a portion of a lead body. Optionally, the mandrel remains with the electrode assembly. If not, the molding material may also flow into the lumen 1148. The arrangement is removed from the mold. The resulting arrangement is optionally ground (e.g., by centerless grinding) to remove the alignment tabs 1143 and part of the lead body resulting in the lead with exposed stimulation surfaces of the segmented electrodes.

Figures 13A, 13B, 13C, 13D:
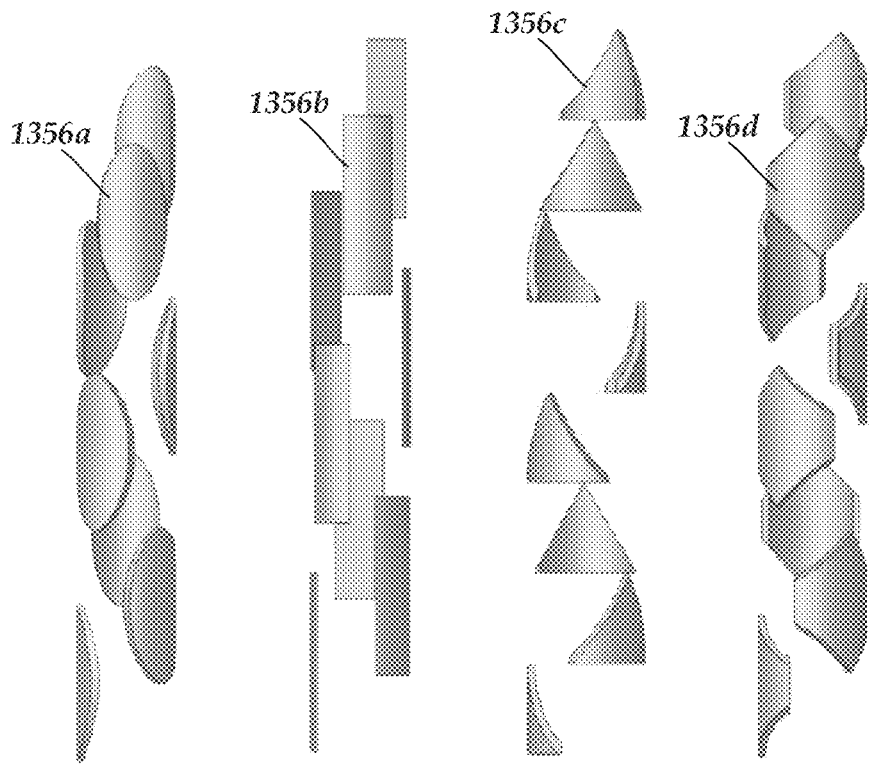
FIG. 13A is a schematic side view of circular or oval segmented electrodes arranged in a single or double helix with the lead body removed for clarity of illustration, according to the invention.
FIG. 13B is a schematic side view of rectangular segmented electrodes arranged in a single or double helix with the lead body removed for clarity of illustration, according to the invention.
FIG. 13C is a schematic side view of triangular segmented electrodes arranged in a single or double helix with the lead body removed for clarity of illustration, according to the invention.
FIG. 13D is a schematic side view of hexagonal segmented electrodes arranged in a single or double helix with the lead body removed for clarity of illustration, according to the invention.
Figures 13E, 13F, 13G:
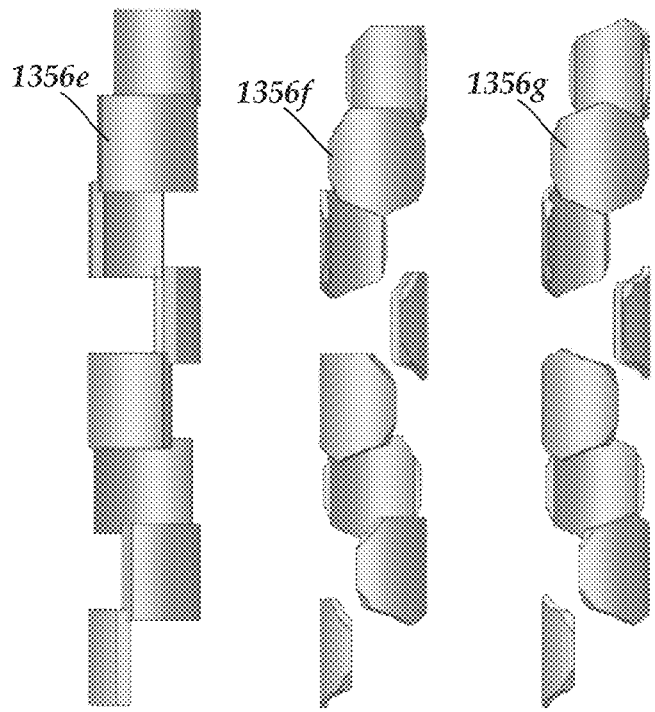
FIG. 13E is a schematic side view of square segmented electrodes arranged in a single or double helix with the lead body removed for clarity of illustration, according to the invention.
FIG. 13F is a schematic side view of octagonal segmented electrodes arranged in a single or double helix with the lead body removed for clarity of illustration, according to the invention.
FIG. 13G is a schematic side view of decagonal segmented electrodes arranged in a single or double helix with the lead body removed for clarity of illustration, according to the invention.

FIGS. 13A-13G illustrate alternative segmented electrode shapes arranged in a double helix with the lead body removed for clarity of illustration. It will be understood that the segmented electrode can have a variety of shapes. For example, the segmented electrodes 1356a of FIG. 13A can be circular or oval in shape. (It will be understood that the shape of the segmented electrodes of FIGS. 13A-13G is described ignoring the curvature of the segmented electrodes around the circumference of the lead for ease of description.) In FIG. 13B, the segmented electrodes 1356b are rectangular in shape. In FIG. 13C, the segmented electrodes 1356c are triangular in shape. In FIG. 13D, the segmented electrodes 1356d are hexagonal in shape, although it will be recognized that the segmented electrodes could also be formed with hexagonal sides that are equal in length or formed as a diamond. In FIG. 13E, the segmented electrodes 1356e are square in shape. In FIG. 13F, the segmented electrodes 1356f are octagonal in shape. In FIG. 13G, the segmented electrodes 1356g have decagonal in shape. It will be recognized that many of shapes, both regular and irregular, are possible. Any of these electrodes can be used in the leads and methods described herein. Moreover, it will be understood that ring electrodes or a tip electrode can be added to any of the electrode arrangements described herein. For example, ring electrodes can be included distal to or proximal to any of the helical segmented electrode arrangements described herein and a tip electrode can be included distal to any of the helical segmented electrode arrangements described herein.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of making a stimulation lead, the method comprising:
   forming a rib framework comprising a plurality of pre-electrodes attached together in a single helix or a double helix, wherein the rib framework comprises at least one alignment tab;
   attaching a conductor to each of the pre-electrodes;
   disposing the rib framework into a mold with the at least one alignment tab of the rib framework disposed in a corresponding slot of the mold;
   forming a lead body between the pre-electrodes; and
   removing a portion of the lead body and the pre-electrodes to generate a plurality of separated segmented electrodes arranged in the single helix or the double helix, wherein each of the pre-electrodes has a greater thickness at a portion of the pre-electrode corresponding to the segmented electrode and a smaller thickness at the portion of the pre-electrode that is removed.

2. The method of claim 1, wherein forming a rib framework comprises forming the rib framework with the pre-electrodes attached to each other at corners of the pre-electrodes.

3. The method of claim 1, wherein forming a rib framework comprises forming the rib framework with the pre-electrodes attached to a helically wound ribbon.

4. The method of claim 1, wherein forming a rib framework comprises forming the rib framework with the pre-electrodes attached to a half-cylinder.

5. The method of claim 4, further comprising forming a cylindrical rib assembly from two of the rib frameworks, wherein disposing the rib framework into the mold comprises disposing the cylindrical rib assembly into the mold.

6. The method of claim 1, further comprising forming a rib assembly from two of the rib frameworks arranged to provide a double helix of the pre-electrodes, wherein disposing the rib framework into the mold comprises disposing the rib assembly into the mold.

7. A method of making a stimulation lead, the method comprising:
- disposing a plurality of segmented electrodes and conductors in a first mold;
- attaching each of the conductors to one of the segmented electrodes;
- molding a carrier over the segmented electrodes using the first mold and forming a plurality of notches on a surface of the carrier opposite the segmented electrodes, wherein each of the notches extends an entire longitudinal length of the carrier and is parallel to the conductors;
- rolling the carrier with the segmented electrodes into a cylinder, wherein the segmented electrodes are arranged in the first mold so that when rolled into a cylinder with the carrier, the segmented electrodes are arranged in a single helix or a double helix;
- placing the cylinder into a second mold; and
- molding a lead body between the segmented electrodes using the second mold.

8. The method of claim 7, wherein the notches and conductors are arranged in an alternating pattern.

9. The method of claim 7, further comprising placing an over tube over the cylinder prior to placing the cylinder into the second mold.

10. A method of making a stimulation lead, the method comprising:
- providing a plurality of segmented electrodes and a plurality of non-conductive spacers, wherein each of the segmented electrode comprises at least one alignment tab and each of the spacers comprises at least one notch;
- forming an electrode assembly by alternating the segmented electrodes with the non-conductive spacers with each of the at least one alignment tab of each of the segmented electrodes disposed in one of the at least one notch of the spacers, wherein each of the spacers is shaped to receive, and fit around a portion of, at least one of the segmented electrodes, wherein the segmented electrodes are positioned in the electrode assembly in a single helix or a double helix;
- placing the electrode assembly into a mold;
- molding a lead body; and
- removing the at least one alignment tab from each of the segmented electrodes after molding the lead body.

11. The method of claim 10, wherein each of the spacers is shaped differently from the other spacers.

12. The method of claim 10, wherein each of the spacers comprises an aligning rib and wherein forming an electrode assembly comprises alternating the segmented electrodes with the non-conductive spacers with the aligning rib of each spacer aligned with the aligning ribs of the other spacers.

13. The method of claim 1, wherein forming a rib framework comprises forming the rib framework with the pre-electrodes attached to an interior surface of a helically wound ribbon.

14. The method of claim 13, wherein the at least one alignment tab is disposed on an outer surface of the helically wound ribbon.

15. The method claim 10, wherein each of the segmented electrodes has a perimeter and each of the spacers is configured and arranged to fit around at least a portion of the perimeter of at least one of the segmented electrodes.

16. The method of claim 10, wherein each of the segmented electrode comprises two alignment tabs and each of the spacers comprises at least one notch, wherein forming an electrode assembly comprises alternating the segmented electrodes with the non-conductive spacers with the two alignment tabs of each of the segmented electrodes disposed in one of the at least one notch of two different ones of the spacers.

* * * * *